United States Patent [19]

Bleek et al.

[11] Patent Number: 5,195,358

[45] Date of Patent: Mar. 23, 1993

[54] APPARATUS FOR MEASURING WATER-VAPOR PARTIAL PRESSURE

[75] Inventors: Ulrich Bleek, Babelsberg; Axel Obiera, Potsdam, both of Fed. Rep. of Germany

[73] Assignee: Wilhelm Lambrecht GmbH, Gottingen, Fed. Rep. of Germany

[21] Appl. No.: 781,369

[22] Filed: Oct. 23, 1991

[30] Foreign Application Priority Data

Oct. 26, 1990 [DE] Fed. Rep. of Germany ....... 4034185

[51] Int. Cl.[5] ............................................. G01N 31/00
[52] U.S. Cl. ................... 73/25.04; 73/29.02; 73/335.02; 73/335.05
[58] Field of Search ................. 73/25.04, 29.01, 29.02, 73/29.05, 31.01, 335, 336.5, 25.05, 31.05, 335.02, 335.03; 204/408, 409, 430, 402

[56] References Cited

U.S. PATENT DOCUMENTS

| | | | |
|---|---|---|---|
| 2,494,628 | 1/1950 | Oberding | 73/335 |
| 2,756,295 | 7/1956 | Schluchter | 73/335 |
| 3,516,282 | 6/1970 | Leach et al. | 73/336.5 |

FOREIGN PATENT DOCUMENTS

| | | |
|---|---|---|
| 1598993 | 9/1974 | Fed. Rep. of Germany . |
| 2416179 | 10/1975 | Fed. Rep. of Germany . |
| 3633016 | 4/1988 | Fed. Rep. of Germany . |
| 523338 | 7/1976 | U.S.S.R. ............... 73/336.5 |
| 696361 | 11/1979 | U.S.S.R. ............... 73/336.5 |

Primary Examiner—Hezron E. Williams
Assistant Examiner—Michael Brock
Attorney, Agent, or Firm—Hopkins & Thomas

[57] ABSTRACT

An apparatus (1) for measuring the water-vapor partial pressure in mixtures of water vapor and gases has an electrolytic cell (18), a measuring sensor (11) determining the temperature of the electrolyte (20), and a heater (23). The cell (18) is subjected to an alternating voltage bringing about no notable heating. The alternating current induced by the alternating voltage controls the heating output of the heater (23). The measuring sensor (11) is arranged in direct thermal contact with the electrolyte (20). The heater (23) is geometrically so extensive in comparison with the cell (18) that a homogeneous radiation field is produced over the entire cell (18). The heater (23) is arranged in relation to a guide for the mixture on the one hand and the cell (18) on the other hand in such a way that the mixture is essentially heated by convection and the electrolyte (20) is essentially heated by radiation.

20 Claims, 3 Drawing Sheets

APPARATUS FOR MEASURING WATER-VAPOR PARTIAL PRESSURE

FIELD OF THE INVENTION

The invention relates to an apparatus for measuring the water-vapor partial pressure in mixtures of water vapor and gases, having an electrolytic cell, a measuring sensor determining the temperature of the electrolyte, and a heater, there being applied to the cell an alternating voltage bringing about no notable heating, the alternating current induced by the alternating voltage controlling the heating output of the heater, and the measuring sensor being arranged in direct thermal contact with the electrolyte. In this context, a measuring sensor is to be understood as the unit comprising a temperature-sensitive element and an enclosure. The enclosure serves here to protect the temperature-sensitive element against mechanical, electrical and chemical influences.

BACKGROUND OF THE INVENTION

The conductivity of an electrolyte depends on the relative concentration of the water. At low humidity concentrations, it is so that the conductivity increases with the water content. If the electrolyte is heated in dependence on its conductivity, part of its water content evaporates. This process continues until the electrolyte is waterless, unless the electrolyte can absorb water vapor from the surroundings. If the electrolyte is surrounded by a mixture of water vapor and gases, ultimately an equilibrium between the amount of water vapor given off and the amount of water vapor taken up establishes itself. This equilibrium is characterized by a certain temperature of the electrolyte. This temperature is a direct measure of the water-vapor partial pressure in the mixture of water vapor and gases.

An apparatus for measuring water-vapor partial pressure having the features described at the beginning is known from German Offenlegungsschrift 2,416,179. There, the heater is in direct thermal contact with the electrolyte and consequently also with the measuring sensor. The electrolyte is therefore heated by heat conduction from the heater. In order to be able to transfer heating output by means of heat conduction, temperature gradients are necessary. In the case of the apparatus according to German Offenlegungsschrift 2,416,179, these temperature gradients lead to undesired effects. The temperature measured as equilibrium temperature is a temperature which actually is only applicable to the heater and not to the electrolyte. The temperature gradient causes a thermotransport in the electrolyte, so that there is no longer homogeneous, and consequently defined, distribution of the electrolyte. The overall equilibrium which has to be achieved for measuring the water-vapor partial pressure also requires that the mixture surrounding the electrolyte is at the equilibrium temperature. Since this mixture is in this case heated indirectly by means of the electrolyte alone, there is only a very small boundary layer of the mixture which is also in equilibrium. All these effects have the result that the apparatus according to German Offenlegungsschrift 2,416,179 proves to be technically complex in terms of control. Even if only slightly maladjusted, it exhibits an unsatisfactory transient response. The state of equilibrium is only achieved after long periods or not at all.

German Patent 1,598,993 discloses an apparatus for measuring water-vapor partial pressure which differs from the type described at the beginning in that the measuring sensor is not arranged in direct thermal contact with the electrolyte. The heater is also neither in direct thermal contact with the electrolyte nor with the measuring sensor. The thermal contact between the measuring sensor, the electrolyte and the heater is brought about by the mixture of water vapor and gases. In order to obtain the equilibrium temperature at all points of the measuring apparatus, a motor is provided for forced circulation of the mixture. The heating of the electrolyte is consequently performed indirectly. The heater heats the mixture, the motor circulates the mixture, the latter comes into the proximity of the electrolyte and there gives off again part of the amount of heat taken up. The comparison of the temperature between the electrolyte and the measuring sensor takes place similarly. In order to achieve a homogeneous temperature distribution within the apparatus, it is necessary in the case of an apparatus according to German Patent 1,598,993 to perform a turbulent forced circulation of the mixture. Otherwise, the temperature differences between the mixture and the electrolyte become great. These temperature differences are then, however, also likely to exist between the electrolyte and the measuring sensor and are thus to be assumed as a measure of the inaccuracy of the measured water-vapor partial pressure. The turbulent forced circulation of the mixture also results in the heater itself not being able to be at a significantly higher temperature than the other component parts of the apparatus. Consequently, heat transfer from the heater to the electrolyte takes place exclusively via the mixture, i.e. by means of convection. The turbulent forced circulation of the mixture entails very serious disadvantages. The necessary motor reduces the reliability of the apparatus. Due to the air flows at the surface of the electrolyte, the latter is eroded. The reaction rate between aggressive agents contained in the mixture and the electrolyte is greatly increased, since the maximum concentration of aggressive agents is always on the surface of the electrolyte. In the case of a static mixture, the electrolyte reacts only with the quantities of aggressive agents in its vicinity, the reaction rate decreasing with time. The quantities of aggressive agents in the direct vicinity of the electrolyte are consumed. Further aggressive agent can diffuse to the surface of the electrolyte only slowly. The electrolyte is also carried away directly by the turbulent forced circulation of the mixture. Small droplets or crystallites are entrained at the surface by the mixture flowing past. The electrolyte is thus distributed throughout the entire apparatus. This has the result that the cell has to be frequently charged with the electrolyte. All of this stands in the way of using the apparatus according to German Patent 1,598,993 for long-term measurements. Apparatuses for measuring watervapor partial pressure are used predominantly for meteorological purposes. Frequently they operate in weather huts which are checked only at intervals of several months.

It is known from both of the abovementioned publications to use lithium chloride as electrolyte for the electrolytic cell. The construction of the electrolytic cell is also disclosed there. The cell has a tubular fabric impregnated with electrolyte, on the surface of which fabric a pair of wire electrodes of noble metal is wound in bifilar and equidistant fashion.

SUMMARY OF THE INVENTION

The invention is based on the object of further developing an apparatus for measuring water-vapor partial pressure of the type described at the beginning in such a way that a high measuring accuracy can be ensured at the same time as great long-term reliability.

According to the invention, this is achieved by the heater being geometrically so extensive in comparison with the cell that a homogeneous radiation field is produced over the entire cell, and by the heater being arranged in relation to a guide for the mixture on the one hand and the cell on the other hand in such a way that the mixture is essentially heated by convection and the electrolyte is essentially heated by radiation. The heater transfers its heating output via two different paths to the electrolyte and the mixture. The electrolyte is heated by radiation. By means of heat radiation, it is possible to transfer quite considerable quantities of heat in a short time. Although a pronounced temperature difference between the heater on the one hand and the electrolyte on the other hand is necessary for this, this does not have adverse effects since the heater is not in direct thermal contact with the electrolyte or the measuring sensor. In addition, heat radiation has the advantage that, as a rule, it is not absorbed by gases. The heat radiation can therefore pass through the mixture and act undiminished on the electrolyte. In order to heat the electrolyte essentially by the radiation, it is self-evident to arrange the heater at a certain distance from it. The mixture of water vapor and gases, on the other hand, is heated by direct contact with the heater. The heated parts of the mixture mix with the non-heated parts, so that the complete mixture is brought to a higher temperature by natural convection. The flows occurring thereby are laminar and extend essentially in the vicinity of the heater. The flow at the surface of the electrolyte is at a minimum which is just sufficient to carry out the mixture exchange necessary for a continuous measurement of the water-vapor partial pressure. The electrolyte is affected as little as possible by this exchange. This gives the electrolyte a considerable service life. Influences due to aggressive agents which can falsify the measuring result do not occur until after very long times. These times are far in excess of half a year. The novel apparatus proves to be technically uncomplicated in terms of control. This is attributable in particular to the stable equilibrium boundary layer in the mixture at the boundary with the electrolyte. This boundary layer is not influenced by the radiation by which the electrolyte is heated. The radiation passes through the boundary layer without giving off heating output. The stable equilibrium boundary layer results in a transient response which can be calculated well. The transient response is characterized by small time constants, i.e. the state of equilibrium can be achieved after only short times. No moving parts are used in the novel apparatus. This avoids undesired loss of reliability. It goes without saying that, if the temperature-sensitive element of the measuring sensor exceeds in its dimensions those of the electrolytic cell, the temperature-sensitive element must also be arranged in the region of homogeneity of the radiation field of the heater. Otherwise, incorrect measurements of the temperature would be preprogrammed. The temperature difference between the heater and the electrolyte which is necessary for sufficient radiation depends on the distance of the heater from the electrolyte. Usually, temperature differences of about 100 kelvins are involved for the desired effect.

The electrolyte may be lithium chloride. Lithium chloride has proved to be particularly suitable for apparatuses for measuring water-vapor partial pressure with an electrolytic cell.

The cell may have a glass fiber layer which is impregnated with the electrolyte and on the surface of which a pair of electrodes of noble metal wire wound in bifilar and equidistant fashion is arranged. Such a design of the electrolytic cell has proved successful due to its simple construction and its reliability.

The measuring sensor may be rod-shaped, the cell being arranged annularly and coaxially on the rod-shaped measuring sensor, the heater coaxially surrounding the measuring sensor, and the rod axis of the measuring sensor running parallel to the force of gravity. In this way, a cylindrical overall construction is achieved. Thus, on the one hand the geometrical requirements for the radiation field can be easily met, on the other hand the flow field of the mixture heated by the heater is also symmetrical with respect to the cell and consequently with respect to the electrolyte.

The heater may have heating wires or heating strips which are arranged equidistantly to one another and parallel to the rod axis of the measuring sensor on a cylinder envelope. With heating wires or heating strips, a heater with which the necessary temperatures can be quickly reached can be realized without problems. The arrangement of the heating strips meets the requirements for the geometry of the radiation field.

The heater may be surrounded by a coaxial tube closed at both ends and provided with break-throughs, in turn a coaxial mixture guiding tube being arranged around this tube. With this arrangement, a chimney effect can be used for the necessary throughput of mixture through the apparatus. The mixture heated by the heater rises and, on leaving the apparatus, draws new mixture into the latter. By the arrangement of the tube surrounding the heater and of the mixture guiding tube, the flow of mixture through the apparatus is apparatus divided into two part-streams. The main stream goes through the apparatus, without being involved in the measuring operation. It provides only the quantities of mixture which serve for measurement in a part-stream. The part-stream enters through the break-throughs into the tube surrounding the heater and passes by means of natural convection and diffusion to the surface of the electrolyte. The part-stream is characterized by a slow movement. The break-throughs can, of course, also be provided at the two closed ends.

The break-throughs, may be axial through-slits. The through-slits are particularly suitable as break-throughs, since they are adapted well to the direction of flow through the apparatus.

Evaluation electronics for the measuring sensor and control electronics for the heater may be arranged inside the guide for the mixture and above the heater. The chimney effect of the heater can be supported by the power dissipation of the evaluation electronics and the control electronics. The power dissipation of the evaluation electronics and control electronics is given off in the form of heat to the mixture. Although this heat dissipation promotes the chimney effect, it does not affect the measurement of the water-vapor partial pressure since, in relation to the mixture stream, the heat dissipation takes place downstream of the measurement of the water-vapor partial pressure.

The evaluation electronics or control electronics may have an additional load. In the case of evaluation electronics or control electronics of low power dissipation, it may be advisable to increase the chimney effect and consequently the mixture throughput through the apparatus by an additional load with appropriate heat dissipation.

The measuring sensor may have a platinum precision resistor as temperature-sensitive element. A platinum precision resistor makes possible output signals which can be evaluated particularly well for temperature determination.

BRIEF DESCRIPTION OF THE DRAWINGS

The invention is explained and described in more detail below with reference to a number of illustrative embodiments. In the drawing.

DETAILED DESCRIPTION

Figure 1:
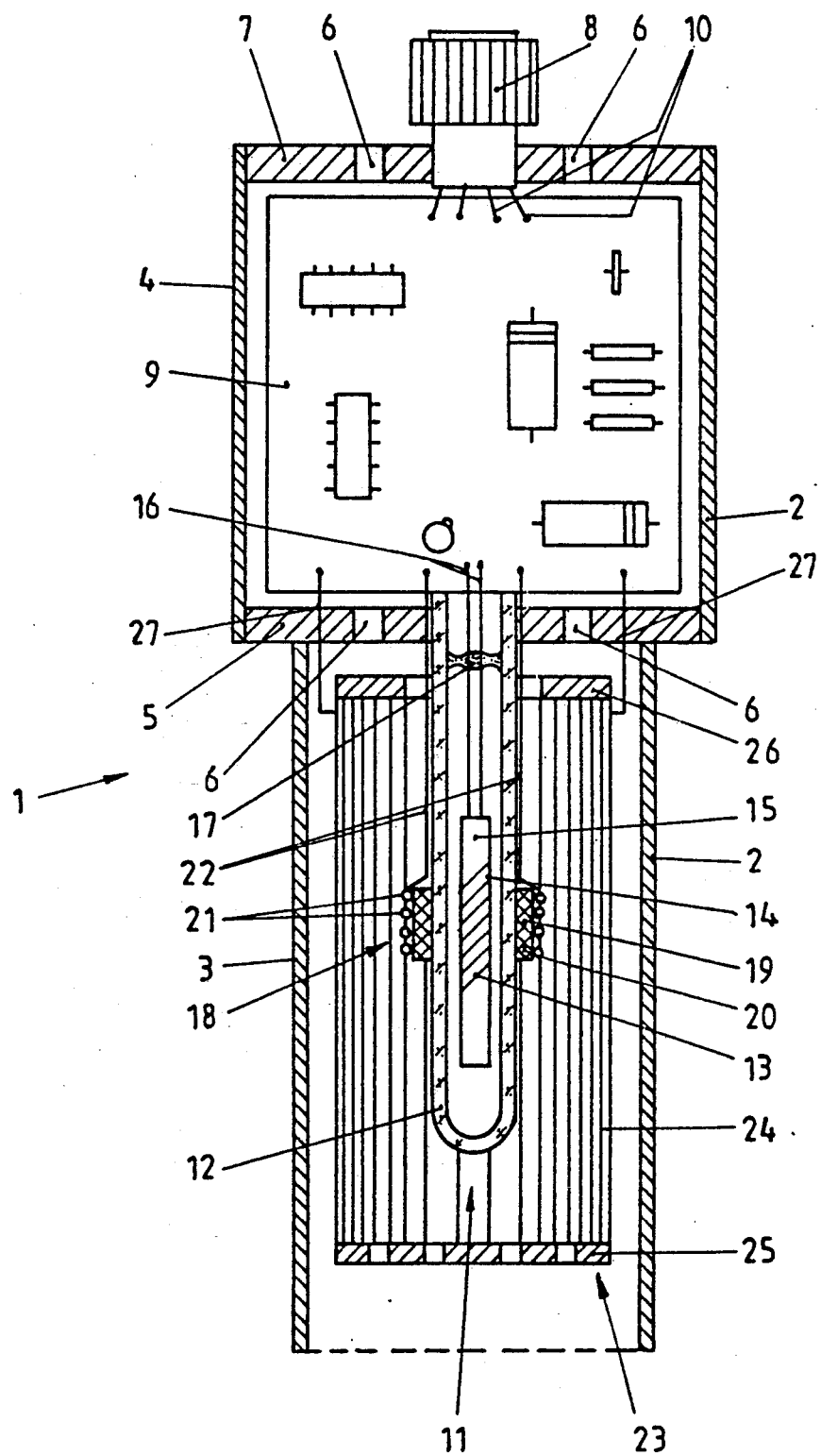
FIG. 1 shows a first embodiment of the apparatus in cross section.

The embodiment of the apparatus 1 represented in FIG. 1 has a rotationally symmetrical housing 2 which is divided into a mixture guiding tube 3 and a tube section 4. During operation of the apparatus 1, the axis of symmetry of the apparatus 1 runs parallel to the force of gravity. The mixture guiding tube 3 is open at its lower end. At its upper end, it is fastened to the connecting plate 5. The connecting plate 5 closes the mixture guiding tube 3 apart from a few through-openings 6. The inner space of the mixture guiding tube 3 is connected by the through-openings 6 to the inner space of the tube section 4. The tube section 4 is likewise fastened to the connecting plate 5 and is substantially closed at its lower end by the connecting plate. The upper end of the tube section 4 is covered virtually completely by a covering plate 7. Just like the connecting plate 5, the covering plate 7 has the through-openings 6. Mounted in the covering plate 7 is a connecting piece 8. The connecting piece 8 serves for connecting the apparatus 1 to a recording unit (not shown here) for the measured values and a voltage source. The design of the connecting piece 8 is such that it coincides with that of conventional apparatuses for measuring water-vapor partial pressure. Via the connecting piece 8, the apparatus 1 is also supplied with electric energy. Underneath the covering plate 7 there is inside the tube section 4 a circuit board 9. The circuit board 9 is connected via leads 10 to the connecting piece 8.

A measuring sensor 11 is arranged inside the mixture guiding tube 3. The measuring sensor 11 is rod-shaped in its outer dimensions and its rod axis coincides with the axis of symmetry of the mixture guiding tube 3. The measuring sensor 11 has a glass tube 12, which is mounted in the connecting plate 5. At its lower end, remote from the connecting plate 5, the glass tube 12 is hermetically sealed. The glass tube 12 does not protrude significantly through the connecting plate 5 into the tube section 4. Inside the glass tube 12 there is a temperature-sensitive element 13. The present apparatus has as temperature-sensitive element 13 a platinum precision resistor 14, which is wound as a thin wire on a support 15. The platinum precision resistor 14 is connected via measuring leads 16 to the circuit board 9. The measuring leads 16 are fixed by a cemented joint 17 inside the glass tube 12. The cemented joint 17 seals off the inside of the glass tube 12 air-tightly. The platinum precision resistor 14 is thus protected all around against electrical, chemical and mechanical effects. A measuring sensor 11 of such a design corresponds as a whole to a commercially available component. Arranged on the outside wall of the glass tube 12 is an electrolytic cell 18. The electrolytic cell 18 has a tubular glass fabric layer 19. The glass fabric layer 19 extends symmetrically with respect to the extent of the temperature-sensitive element 13. It is impregnated with an electrolyte 20. On the surface of the glass fabric layer 19 there is a pair of electrodes 21, which consists of noble metal wire wound in bifilar and equidistant fashion. The pair of electrodes 21 is connected via supply leads 22 to the circuit board 9. The electrolytic cell 18 and the measuring sensor 11 are coaxially surrounded by a heater 23. The heater 23 has a continuous heating wire 24, which is stretched back and forth many times between a lower holding plate 25 and an upper holding plate 26. The heating wire 24 thereby runs in each case on the cylinder envelope of an imaginary cylinder, parallel to the axis of the latter. The axis of the imaginary cylinder coincides with the rod axis of the measuring sensor. The heating wire is connected via supply leads 27 to the circuit board. The lower holding plate 25 partially shields the electrolytic cell 18 in the downward direction. The upper holding plate 26 does not perform any separate shielding function.

The operating principle of the apparatus 1 is based on the conductivity of the electrolyte 20 in the electrolytic cell 18. The conductivity of the electrolyte 20 depends on its relative water content. The water content of the electrolyte 20 used as a reference is low, so that the conductivity of the electrolyte 20 increases with the relative water content. The conductivity of the electrolyte 20 in the electrolytic cell 18 is determined by means of the pair of electrodes 21. The pair of electrodes 21 is subjected via the supply leads 22 to an alternating voltage from the circuit board 9, which is so low that it does not bring about any significant heating of the electrolyte. The current through the electrolyte induced by the alternating voltage between the pair of electrodes 21 is a direct measure of the conductivity of the electrolyte 20. This current through the electrolyte also flows through the supply leads 22 of the pair of electrodes 21. On the circuit board 9 there are control electronics which, dependent on the current through the electrolyte, control a current which flows via the supply leads 27 through the heating wire 24. The heat radiation emanating from the heating wire 24 acts on the electrolyte 20 in the electrolytic cell 18, so that the electrolyte 20 heats up. As a result, part of the water content of the electrolyte 20 evaporates and the conductivity of the electrolyte decreases. With the decreasing conductivity, the radiation output of the heating wire 34 is also reduced, and consequently so is the heating rate of the electrolyte 20. These processes alone would result in an albeit slowing, but ultimately complete drying out of the electrolyte 20. However, the electrolyte 20 constantly takes up water vapor from its surroundings. The surroundings of the electrolyte 20 may be any mixture of water vapor and gases, but as a rule it is air. The water-vapor partial pressure in the mixture determines the rate at which the electrolyte can take up moisture from its surroundings. Ultimately, an equilibrium between the quantity of moisture given off and the quantity of moisture taken up will be established in the electrolyte. This equilibrium is characterized by a certain temperature. The region of the equilibrium temperature in this case extends over the electrolytic cell 18, the measuring sensor 11 or at least the temperature-sensitive element 13 and a boundary layer of the mixture which surrounds the electrolyte 20. The heating of this boundary layer takes place only in small part by the electrolyte. The heating of the boundary layer takes place predominantly by the mixture being heated by the heating wire 24 before it comes into the vicinity of the electrolyte 20. Whereas the electrolyte 20 is essentially heated by means of the heat radiation emanating from the heating wire 24, the heating of the mixture takes place with the assistance of the direct heat transfer from the heating wire and the resultant natural convection. The natural convection induced by the heating wire also brings about the mixture throughput through the apparatus 1. The apparatus 1 as a whole forms a type of chimney, in which the heating wire 24 of the heater 23 heats the mixture, which thereupon rises and passes through the through-openings 6, first of all into the tube section 4 and then out of the apparatus 1, new mixture being sucked in. The chimney effect is intensified by the power dissipation of the control electronics for the heater 23 and the evaluation electronics for the measuring sensor 11. To achieve an increased throughput of mixture, it may be advisable to provide on the circuit board 9 an additional load which is distinguished by a high power dissipation. An incandescent bulb would be suitable, for example. The measured value supplied by the apparatus 1 corresponds to the equilibrium temperature of the electrolyte 20 with respect to a certain water-vapor partial pressure in the mixture surrounding the electrolyte 20. The equilibrium temperature is determined by the electrical resistance of the platinum precision resistor 14 with the assistance of the measuring leads 16. Evaluation electronics are provided on the circuit board for this purpose. The measured values are passed on via the leads 10 and the connecting piece 8, connected to them, to the recording unit (not shown here).

The flow of the mixture at the surface of the electrolyte 20 is caused only by natural convection. The flow is laminar and a boundary layer of the mixture around the electrolyte, in equilibrium with the electrolyte, can be ensured in adequate thickness at all times.

Figure 2:
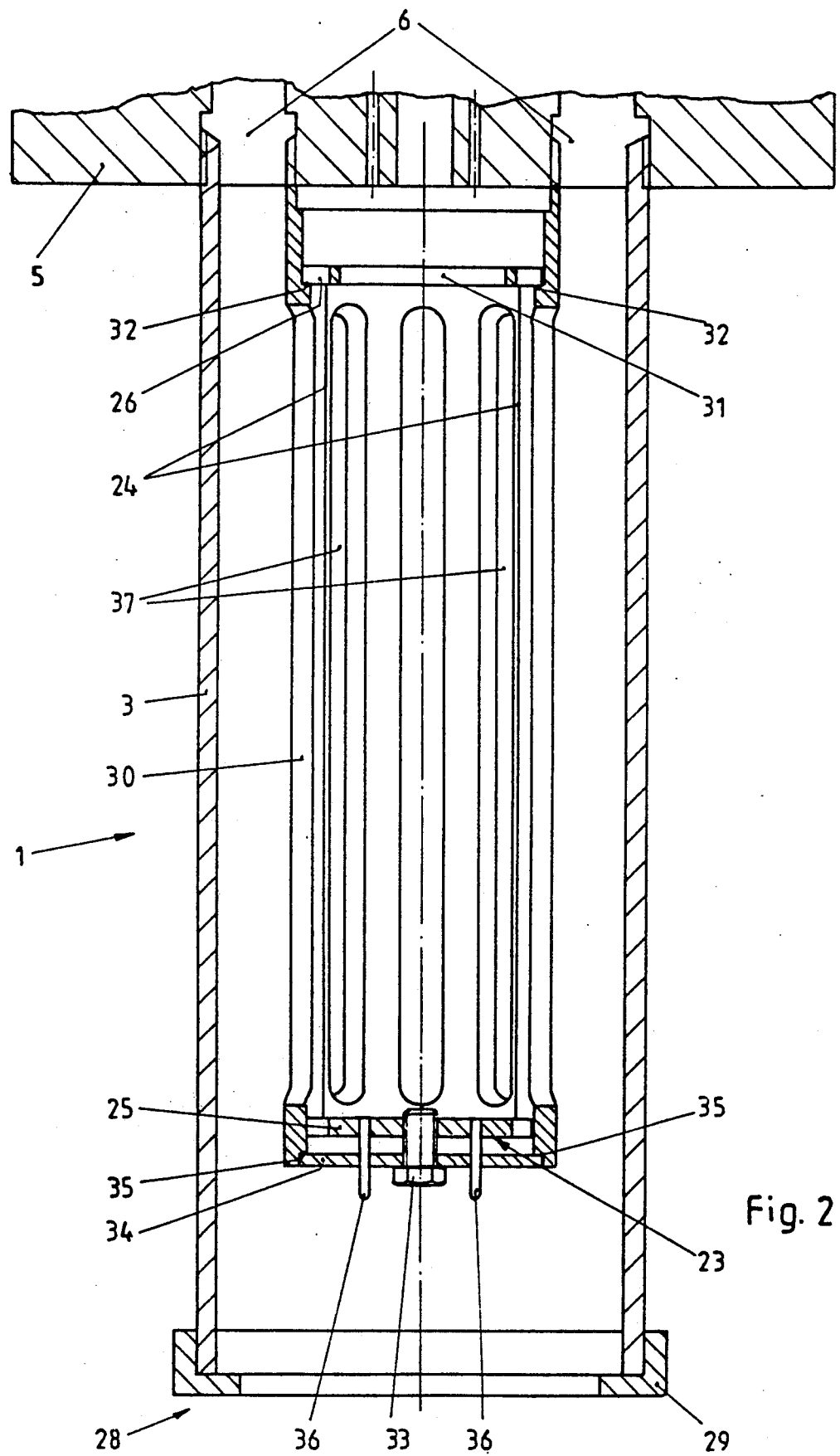
FIG. 2 shows the detail view of a second embodiment of the apparatus.

FIG. 2 shows the detail of a second embodiment of the apparatus 1, which differs from the embodiment according to FIG. 1 only in the constructional elements shown here. The mixture guiding tube 3 is screwed into the connecting plate 5. The lower end of the mixture guiding tube 3 is closed off by a cover 28, which has a holding ring 29 and a fly grid (not shown here) in the opening of the latter. The fly grid is intended to keep insects away from the inside of the apparatus 1. The fly grid hinders only insignificantly the throughput of mixture of which the water-vapor partial pressure is to be measured. Arranged inside the mixture guiding tube 3 is a tube 30, coaxial to the latter. The tube 30 is likewise screwed into the connecting plate 5. The tube 30 serves for mounting the lower holding plate 25 and upper holding plate 26 for the heating wire 24. The lower holding plate 25 and the upper holding plate 26 are designed as gear wheels with rectangular teeth. The heating wire 24 in each case leads above the upper holding plate 26 or below the lower holding plate 25 around these teeth. The upper holding plate 26 has a central opening 31, through which the measuring sensor 11 with the electrolytic cell 18 according to FIG. 1 protrudes into the heater 23. The upper holding plate 26 bears against a peripheral shoulder 32 inside the tube 30. The lower holding plate 25 is held by a screw 33, which is supported on a counter-plate 34. The counter-plate 34 bears against the peripheral projection 35 inside the tube 30. The peripheral projection 35 corresponds to the peripheral shoulder 32, against which the upper holding plate 26 bears. By turning the screw 33, the distance of the lower holding plate 25 from the upper holding plate 26 can be varied. Consequently, the heating wire 24 can be tensioned by turning the screw 33. Thus, the two holding plates 25, 26 and the counter-plate 34 are also given a completely defined position. Connected to the lower holding plate 25 are connections 36 for the heating wire 24. The connections 36 protrude through the counter-plate 34. The supply leads 27 for the heater 23 according to FIG. 1 are to be fastened to the connections 36.

The tube 30 performs several functions. Firstly, it serves as support for the heater 23, secondly it performs the task of a reflector for the radiation emanating from the heating wire 24 onto the axis of symmetry of the tube 30 and consequently the electrolytic cell 18 according to FIG. 1. Furthermore, the tube 30 divides the stream of mixture through the apparatus 1 into two part-streams. The main stream passes only through the mixture guiding tube 3, but not through the tube 30. It enters through the fly grid in the cover 28 into the tube 3 and leaves the latter through the openings 6 in the connecting plate 5. From the main stream, a part-stream is fed, which enters through axial throughslits 37 into the tube 30. The mixture is thereby taken closely past the heating wire 24 and thus heated before it can reach the electrolytic cell 18 and consequently the electrolyte 20 according to FIG. 1. The main stream of the mixture is the basis for the necessary throughput through the apparatus 1; the part-stream serves for the actual measurement of the water-vapor partial pressure and is distinguished by little mixture movement, to maintain favorable measuring conditions.

Figure 3:
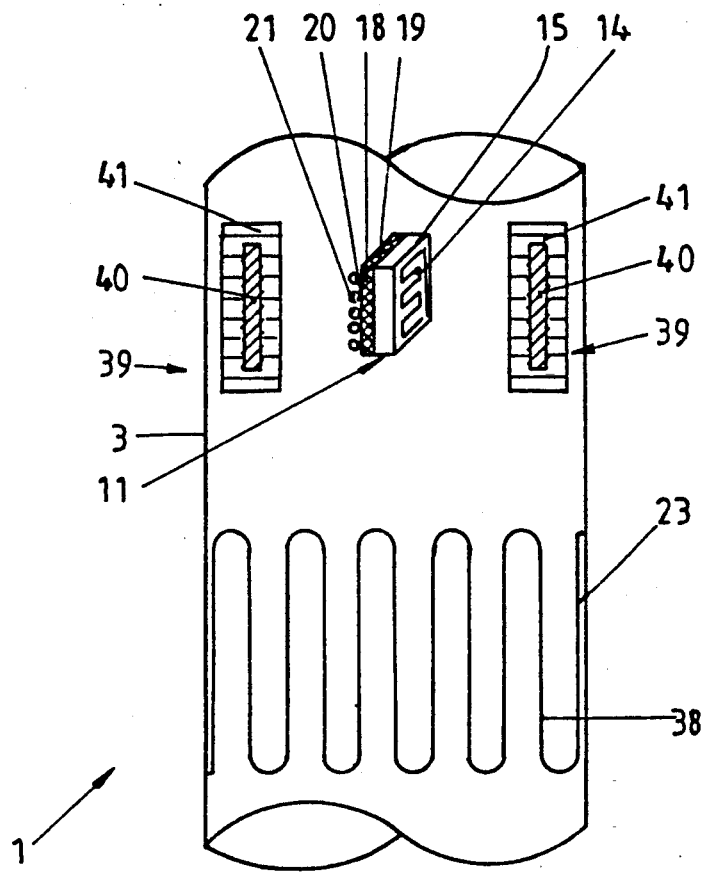
FIG. 3 shows a further embodiment of the apparatus in diagrammatic, perspective representation.

In FIG. 3, an embodiment of the apparatus 1, which differs distinctly from the apparatus 1 according to FIG. 1, is represented perspectively and diagrammatically. The heater 23 is divided here into two separate elements. A heating grid 38 is arranged in the lower region of the mixture guiding tube 3. The electrolytic cell 18 and the measuring sensor 11 surround two heating radiators 39 with heating coils 40 and reflectors 41. Here, the measuring sensor 11 consists of the platinum precision resistor 14, which is cast in the support 15. The support 15 is right-parallelepipedal and aligned with its two major surfaces toward the reflectors 41. Only half of the electrolytic cell 18 is represented. The electrolytic cell 18 has the glass fabric layer 19 impregnated with electrolyte 20, and the pair of electrodes 21. The glass fabric layer 19 in this case extends in each case over the major surface of the support 15. The mixture of which the water-vapor partial pressure is to be determined enters the mixture guiding tube 3 from below. There, it is heated by the heating grid 38. Subsequently, the mixture reaches the surface of the electrolyte 20. The electrolyte 20 is heated by the two heating radiators 41, the radiation field being homogeneous over the extent of the electrolytic cell. In the case of the present design of the apparatus 1, the two modes of action of the heater 35 are also spatially separate. The convective heating of the mixture is performed by the heating grid 38, whereas the heating of the electrolyte by means of radiation is carried out by the heating radiators 39. Instead of the heating radiators 39, other sources of radiation would also be conceivable, such as for example a microwave source.

The preferred embodiments of the invention have been disclosed in detail in the foregoing specification, and it will be understood by people skilled in the art that variations and modifications may be made without departing from the spirit and scope of the invention, as set forth in the following claims.

| List of reference numerals: | |
|---|---|
| 1. Apparatus | 27. Supply leads |
| 2. Housing | 28. Cover |
| 3. Mixture guiding tube | 29. Holding ring |
| 4. Tube section | 30. Tube |
| 5. Connecting plate | 31. Opening |
| 6. Through-openings | 32. Shoulder |
| 7. Covering plate | 33. Screw |
| 8. Connecting piece | 34. Counter-plate |
| 9. Circuit board | 35. Projection |
| 10. Leads | 36. Connections |
| 11. Measuring sensor | 37. Slits |
| 12. Glass tube | 38. Heating grid |
| 13. Temperature-sensitive element | 39. Heating radiator |
| 14. Platinum precision resistor | 40. Heating coil |
| 15. Support | 41. Reflector |
| 16. Measuring leads | |
| 17. Cemented joint | |
| 18. Cell | |
| 19. Glass fabric layer | |
| 20. Electrolyte | |
| 21. Pair of electrodes | |
| 22. Supply leads | |
| 23. Heater | |
| 24. Heating wire | |
| 25. Lower holding plate | |
| 26. Upper holding plate | |

We claim:

1. An apparatus for measuring the water-vapor partial pressure in a mixture of water vapor and gas, the apparatus comprising:
an electrolytic cell having an electrolyte exposed to said mixture and configured to receive an alternating voltage, said alternating voltage configured to induce an alternating current within said electrolytic cell having a magnitude dependent upon said partial pressure;
a measuring sensor in direct thermal contact with said electrolyte of said electrolytic cell, said measuring sensor configured to measure the temperature of said electrolyte;
a heater separated from and surrounding said electrolytic cell thereby defining a space therebetween for passage of said mixture, said heater being controlled by said alternating current, said heater configured to heat said mixture with essentially convection heat, and said heater being geometrically so extensive relative to the cell that a homogeneous radiation field is produced around said electrolytic cell to thereby heat said electrolyte with essentially radiant heat.

2. The apparatus of claim 1, wherein said electrolyte comprises lithium chloride.

3. The apparatus of claim 1, wherein said cell comprises a glass fabric layer impregnated with said electrolyte and having a surface with a pair of electrodes of nobel metal wire wound in bifilar and equidistant fashion.

4. The apparatus of claim 1, wherein said measuring sensor comprises a rod-shaped structure, said cell being arranged annularly and coaxially on said rod-shaped structure, and the rod axis of said measuring sensor running parallel to the force of gravity.

5. The apparatus of claim 4, further comprising a coaxial tube surrounding said heater, said coaxial tube closed at both ends and provided with breakthroughs, and further comprising a guide tube surrounding said coaxial tube, said guide tube configured to guide said mixture.

6. The apparatus of claim 5, wherein said breakthroughs comprise axial through slits.

7. The apparatus of claim 5, further comprising evaluation electronics for receiving signals from said measuring sensor indicative of said temperature of said electrolyte and further comprising control electronics for generating said alternating voltage, for receiving said alternating current, and for controlling the intensity of said heater in response to said alternating current, said evaluation electronics and said control electronics being arranged inside said guide tube for said mixture and above said heater.

8. The apparatus of claim 7, wherein said evaluation electronics comprises an additional load resistance.

9. The apparatus of claim 7, wherein said control electronics comprises an additional load resistance.

10. The apparatus of claim 1, wherein said heater comprises a plurality of heating wires arranged equidistantly to one another and forming a cylinder envelope about said measuring sensor.

11. The apparatus of claim 1, wherein said measuring sensor comprises a platinum precision resistor operating as a temperature sensitive element.

12. An apparatus for measuring the partial pressure in a mixture of water vapor and gas, the apparatus comprising:
an electrolytic cell means for maintaining an electrolyte in contact with said mixture and for receiving an alternating voltage, said alternating voltage for inducing an alternating current within said electrolytic cell having a magnitude dependent upon said partial pressure of said mixture;
a measuring sensor means for monitoring the temperature of said electrolyte of said electrolytic cell;
a heater means for surrounding said electrolytic cell and for defining a space therebetween for passage of said mixture, said heater means being controlled by said alternating current, said heater means for heating said mixture with essentially convection heat, and said heater means for producing a homogeneous radiation field around said electrolytic cell to thereby heat said electrolyte with essentially radiant heat.

13. The apparatus of claim 12, wherein said electrolyte comprises lithium chloride.

14. The apparatus of claim 12, wherein said electrolyte cell means comprises a glass fabric layer impregnated with said electrolyte and having a surface with a pair of electrodes of metal wire wound in bifilar and equidistant fashion.

15. The apparatus of claim 12, wherein said measuring sensor means comprises a rod-shaped structure, said cell means being arranged annularly and coaxially on said rod-shaped structure, and the rod axis of said measuring sensor means running parallel to the force of gravity.

16. The apparatus of claim 15, further comprising a coaxial tube surrounding said heater means, said coaxial tube closed at both ends and provided with breakthroughs, said coaxial tube configured to reflect heat inwardly, and further comprising a guide tube surrounding said coaxial tube, said guide tube configured to guide and confine said mixture.

17. The apparatus of claim 16, wherein said breakthroughs comprise axial throughway slits.

18. The apparatus of claim 16, further comprising evaluation electronic means for receiving signals from said measuring sensor means indicative of said temperature of said electrolyte and further comprising control electronic means for generating said alternating voltage, for receiving said alternating current, and for controlling the intensity of said heater means in response to said alternating current, said evaluation electronic means and said control electronic means being arranged inside said guide tube for said mixture and above said heater means.

19. The apparatus of claim 12, wherein said heater means comprises a plurality of heating wires arranged equidistantly to one another and forming a cylinder envelope about said measuring sensor means.

20. The apparatus of claim 12, wherein said measuring sensor means comprises a platinum precision resistor operating as a temperature sensitive element.

* * * * *